United States Patent
Fournie et al.

(10) Patent No.: US 10,918,343 B2
(45) Date of Patent: Feb. 16, 2021

(54) METHOD FOR MOTION CORRECTION OF SPECTRAL COMPUTED TOMOGRAPHY DATA AND AN ENERGY-SENSITIVE COMPUTED TOMOGRAPHY DEVICE

(71) Applicant: Siemens Healthcare GmbH, Erlangen (DE)

(72) Inventors: Eric Fournie, Erlangen (DE); Steffen Kappler, Effeltrich (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 64 days.

(21) Appl. No.: 16/351,595

(22) Filed: Mar. 13, 2019

(65) Prior Publication Data
US 2019/0282184 A1    Sep. 19, 2019

(30) Foreign Application Priority Data
Mar. 16, 2018 (DE) ............... 10 2018 204 093.1

(51) Int. Cl.
*A61B 6/03* (2006.01)
*A61B 6/00* (2006.01)
(Continued)

(52) U.S. Cl.
CPC .......... *A61B 6/032* (2013.01); *A61B 6/482* (2013.01); *A61B 6/5264* (2013.01);
(Continued)

(58) Field of Classification Search
CPC .......... A61B 6/32; A61B 6/481; A61B 6/482; A61B 6/503; A61B 6/4007; A61B 6/4241;
(Continued)

(56) References Cited

U.S. PATENT DOCUMENTS

6,937,690 B2 * 8/2005 Bruder ............... A61B 6/032 378/15
8,055,050 B2 * 11/2011 Roessl ............... G06T 11/005 382/131
(Continued)

FOREIGN PATENT DOCUMENTS

WO    WO 2017216248 A1    12/2017

OTHER PUBLICATIONS

Bhagalia, Roshni et al.: "Nonrigid registration-based coronary artery motion correction for cardiac computed tomography"; in: Med Phys.; vol. 39, No. 7; pp. 4245-4254; 2012.
(Continued)

*Primary Examiner* — Daniel G Mariam
(74) *Attorney, Agent, or Firm* — Harness, Dickey & Pierce, P.L.C.

(57) ABSTRACT

A method and energy-sensitive CT device are disclosed for motion correction of a computed tomography image. In an embodiment, the method includes: provisioning spectral CT data of an examination region with a moving object, the spectral CT data being recorded with an energy-sensitive CT device and including CT data at at least one energy level, and the at least one energy level of the CT data being adapted to a structure in the moving object; identifying the structure in the CT data at at least one energy level, of the at least one energy level, adapted to the structure; calculating a motion vector field of the structure identified; and motion correcting the spectral CT data by the motion vector field calculated to produce a motion-corrected CT image.

20 Claims, 4 Drawing Sheets

(51) Int. Cl.
G06T 11/00 (2006.01)
H04N 5/232 (2006.01)

(52) U.S. Cl.
CPC ....... *G06T 11/005* (2013.01); *H04N 5/23264* (2013.01); *A61B 6/4007* (2013.01); *A61B 6/4241* (2013.01); *A61B 6/481* (2013.01); *A61B 6/503* (2013.01)

(58) Field of Classification Search
CPC .. A61B 6/5264; G06T 11/005; H04N 5/23264
USPC .......................................... 382/131
See application file for complete search history.

(56) References Cited

U.S. PATENT DOCUMENTS

| | | | |
|---|---|---|---|
| 8,224,056 B2 | 7/2012 | Pack et al. | |
| 10,657,621 B2* | 5/2020 | Brown | G06T 7/11 |
| 2010/0248377 A1* | 9/2010 | Hess | G01N 33/5302 436/86 |
| 2013/0046176 A1* | 2/2013 | Mistretta | A61B 6/4441 600/431 |
| 2016/0345926 A1* | 12/2016 | Dutta | A61B 6/032 |
| 2019/0295249 A1* | 9/2019 | Schaefer | G16H 30/40 |

OTHER PUBLICATIONS

Hahn, Juliane. et al.: "Cardiac Motion Compensation from Short-Scan CT Data: A Comparison of Three Algorithms. In Proceedings of the 4th International Conference on Image Formation in X-Ray Computed Tomography"; Siemens Healthcare GmbH 1. Power Point Präsentation; 2. publication Jul. 18-22, 2016. 2013. pp. 185-188.

Avants, B. B. et al. "Symmetric diffeomorphic image registration with cross-correlation: Evaluating automated labeling of elderly and neurodegenerative brain" Medical Image Analysis, Elsevier, vol. 12, pp. 26-41. 2008; 2008.

Van Stevendaal, U. et al.: "A motion-compensated scheme for helical cone-beam reconstruction in cardiac CT angiography."; in Medical Physics; vol. 35; Issue 7; pp. 3239-3251; Jul. 2008; DOI: 10.1118/1.2938733; 2008.

Sotiras, Aristeidis et al.: "Discrete symmetric image registration"; in 9th IEEE International Symposium on Biomedical Imaging (ISBI); 2012; DOI: 10.1109/ISBI.2012.6235554.

Isola, A., A. et al.: "Cardiac motion-corrected iterative cone-beam CT reconstruction using a semi-automatic minimum cost path-based coronary centerline extraction"; in: Computerized Medical Imaging and Graphics; vol. 36, pp. 215-226; 2012.

Tang, Qiulin et al.: "Motion estimation and compensation for coronary artery and myocardium in cardiac CT"; in: Medical Imaging, San Diego; 2015.

Rohkohl Christopher et al., "Improving best-phase image quality in cardiac CT by motion correction with MAM optimization", in: Medical Physics, vol. 40. No. 3, Mar. 2013, pp. 031901-1 til 031901-15.

Tang, Quiulin et al.: "A fully four-dimensional; iterative motion estimation and compensation method for cardiac CT"; in: Med. Phys.; vol. 39, No. 7; pp. 4291-4305; 2012.

Hahn, Juliane et al.: "Reduction of Motion Artifacts in Cardiac CT based on Partial Angle Reconstructions from Short Scan Data"; in: Medical Imaging; Siemens Healthcare GmbH 1. Power Point Präsentation; 2. publication Physics of Medical Imaging; Feb. 27-Mar. 3, 2016; San Diego; California; United States; Bellingham; Wash.; SPIE; 2016 (Proceedings of SPIE; 9783); p. 97831A-1-97831A-9.; ISBN 978-1-5106-0018-8; DOI: 10.1117/12.2216181.

Kim, Seungeon et al.: "Cardiac motion correction based an partial angle reconstructed images in x-ray CT"; in: Med. Phys.; vol. 42, No. 5, pp. 2560-2571; May 2015; DOI: 10.1118/1.4918580.

Vercauteren, Tom et al.: "Diffeomorphic demons: Efficient non-parametric image registration"; in NeuroImage; vol. 45; pp. 61-72; 2009; doi:10.1016/j.neuroimage.2008.10.040.

German Patent Document TB 100a / 12.14 ; for German Patent Application No. 102018204093.1 dated Nov. 27, 2018.

Boussel, L. et al. "Photon counting spectral CT component analysis of coronary artery atherosclerotic plaque samples" British Journal of Radiology, vol. 87, No. 1040, Aug. 1, 2014 (Aug. 1, 2014)— (Published Online: Jul. 4, 2014) // X ISSN: 0007-1285 // https://doi.org/10.1259/bjr.20130798.

Allec, N. et al. "Including the effect of motion artifacts in noise and performance analysis of dual-energy contrast-enhanced mammography" Physics in Medicine and Biology, Institute of Physics Publishing, vol. 57, No. 24, pp. 8405-8425, Nov. 30, 2012 (Nov. 30, 2012), ISSN: 0031-9155 // DOI: 10.1088/0031-9155/57/24/8405.

Extended European Search Report dated Jul. 10, 2019.
German Office Action dated Oct. 22, 2020.

* cited by examiner

METHOD FOR MOTION CORRECTION OF SPECTRAL COMPUTED TOMOGRAPHY DATA AND AN ENERGY-SENSITIVE COMPUTED TOMOGRAPHY DEVICE

PRIORITY STATEMENT

The present application hereby claims priority under 35 U.S.C. § 119 to German patent application number DE 102018204093.1 filed Mar. 16, 2018, the entire contents of which are hereby incorporated herein by reference.

FIELD

Embodiments of the invention generally relate to a method for motion correction of spectral computed tomography data and an energy-sensitive computed tomography device with which motion-corrected CT images can be generated.

BACKGROUND

Computed tomography imaging is often used in routine clinical practice to visualize cardiovascular diseases since, particularly when using an iodine-containing contrast medium, computed tomography (CT) enables high-resolution and high-contrast visualization of blood vessels. Computed tomography is also used to visualize coronary vessels, but here CT has limitations due to the rapid movement of the heart: even when using an ECG and with appropriate timing of the CT recordings in the phases of the cardiac cycle with less movement (for example, the diastole), it is not at present possible to perform a complete CT scan in a time short enough for the movement of the heart to be irrelevant.

For this reason, a number of methods were developed in the past, such as, for example, those described in the following publications:

R. Bhagalia, J. D. Pack, and J. V. Miller. Nonrigid registration-based coronary artery motion correction for cardiac computed tomography. *Med. Phys.*, July 2012.

J. Hahn, H. Bruder, T. Allmendinger, K. Stierstorfer, T. Flohr, and M. Kacheris. Cardiac Motion Compensation from Short-Scan CT Data: A comparison of Three algorithms. In *Proceedings of the 4th International Conference on Image Formation in X-Ray computed Tomography*, Bamberg, 2016. CT Meeting.

J. Hahn, H. Bruder, T. Allmendinger, K. Stierstorfer, T. Flohr, and M. Kacheris. Reduction of Motion Artifacts in Cardiac CT based on Partial Angle Reconstructions from Short Scan Data. In *Medical Imaging*, San Diego, 2016. SPIE.

A. A. Isola, C. T. Metz, M. Schaap, S. Klein, M. Grass, and W. J. Niessen. Cardiac motion-corrected iterative cone-beam CT reconstruction using a semi-automatic minimum cost path-based coronary centerline extraction. *Computerized Medical Imaging and Graphics*, 2012.

S. Kim, Y. Chang and J. B. Ra. Cardiac motion correction based on partial angle reconstructed images in x-ray CT. *Med. Phys.*, May 2015.

J. D. Pack, P. M. Edic, B. E. H. Claus, M. Iatrou, and J. V. Miller. Method for computed tomography motion estimation and compensation, July 2012. U.S. Pat. No. 8,224,056.

C. Rohkohl, H. Bruder, and K. Stierstorfer. Improving best-phase image quality in cardiac CT by motion correction with MAM optimization. *Med. Phys.*, March 2013.

Q. Tang, J. Cammin, S. Srivastava, and K. Taguchi. A fully four-dimensional, iterative motion estimation and compensation method for cardiac CT. *Med. Phys.*, July 2012.

Q. Tang, J. Matthews, M. Razeto, J. J. Linde, and S. Nakanishi. Motion estimation and compensation for coronary artery and myocardium in cardiac CT. In *Medical imaging*, San Diego, 2015. SPIE U. van Stevendaal, J. von Berg, and M. Grass. A motion-compensated scheme for helical cone-beam reconstruction in angiography. *Med. Phys.*, July 2007.

The content of each of the aforementioned documents, in their entirety, is hereby incorporated herein by reference in the disclosure content of this application.

The transition between several stacks of images is discussed in the following documents:

B. Avants, C. Epstein, M. Grossmann and J. Gee. Symmetric diffeomorphic image registration with cross-correlation: Evaluating automated labeling of elderly and neurodegenerative brain; *Medical Image Analysis*, 2008

A. Sotiras and N. Paragios. Discrete Symmetric Image Registration, In 2012 9th *IEEE International Symposium on Biomedical Imaging (ISBI)*, 2012.

T. Vercauteren, X. Pennec, A. Perchant and N. Ayache. Diffeomorphic demons: Efficient non-parametric image registration, *NeuroImage*, 2009.

The content of each of these additionally mentioned documents, in their entirety, is hereby incorporated herein by reference in the disclosure content of this application.

A common feature of most of these motion-correction algorithms is that the movement of a specific structure in the moving object, for example the vessel filled with contrast medium, is tracked and a motion vector is created therefrom. However, a prerequisite for this is that specific, precisely defined structures can be particularly easily recognized in the motion-distorted image and isolated from their surroundings.

Moreover, it is often necessary to record such a large examination region that it is divided into several stacks of axial images. This may possibly lead to problems due to motion artifacts, i.e. the stacks cannot be assembled correctly because the patient has moved between the recording of the individual stacks.

Some CT devices enable recording of energy-sensitive computed tomography (CT) data, i.e. the CT image only shows the adsorption or attenuation of photons in a specific energy range, hereinafter also called energy level. Since different structures in the body have different mass attenuation coefficients at different photon energies, spectral CT can record several images of the same region with different contrast in one recording.

SUMMARY

At least one embodiment of the invention provides an improved method for motion correction of computed tomography images. In particular, at least one embodiment of the method should improve the possibility of motion correction of CT images in the heart.

Embodiments of the application are directed to a method and a CT device. Advantageous embodiments in the invention are disclosed in the claims.

An embodiment of the application is directed to a method for motion correction of a computed tomography image, comprising:

provisioning spectral CT data of an examination region with a moving object, the spectral CT data being recorded with an energy-sensitive CT device and including CT data at at least one energy level, and the at least one energy level of the CT data being adapted to a structure in the moving object;

identifying the structure in the CT data at the at least one energy level adapted to the structure;

calculating a motion vector field of the structure identified; and motion correcting the spectral CT data by the motion vector field calculated to produce a motion-corrected CT image.

An embodiment of the application is directed to an energy-sensitive CT device, comprising:

at least one processor, configured to provision spectral CT data of an examination region with a moving object, the spectral CT data being recorded with an energy-sensitive CT device and including CT data at at least one energy level, and the at least one energy level of the CT data being adapted to a structure in the moving object, identify the structure in the CT data at the at least one energy level adapted to the structure, calculate a motion vector field of the structure identified, and motion correct the spectral CT data by the motion vector field calculated to produce a motion-corrected CT image.

BRIEF DESCRIPTION OF THE DRAWINGS

The invention is now described in more detail with reference to exemplary embodiments and with reference to the attached drawings, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

Embodiments of the invention are based on the finding that, with spectral CT data, i.e. CT data that only covers a specific energy level or a specific energy range, it is particularly easily possible to identify moving structures in the CT data and use them for motion correction. For example, the CT data can be broken down into the different materials (material decomposition) particularly reliably and without any or, with extremely little, computational effort. Herein, it is, for example, possible to identify and possibly extract iodine-filled vessels or elements of the skeleton that indicate a possible movement of the patient or the moving organ. This enables the motion correction methods described in the prior art to be greatly simplified because complex and error-prone segmentation of the motion-contaminated image volumes in order to isolate such structures is no longer necessary.

The method of at least one embodiment includes the provision of spectral CT data of an examination region with a moving object, wherein the spectral CT data was recorded with an energy-sensitive CT device. The energy-sensitive CT device of at least one embodiment can be any CT device that is available at present or will be available in future that allows CT data at one or more specific energy levels to be recorded separately of one another. Examples include dual-energy, or dual-source or fast-switching technologies, as discussed below.

An examination region may be, for example, the field of view of a CT examination, in particular a section of the human or animal body. The moving object can be the human heart, but also the thorax or any other organ or part of the human or animal body because any body part can move during the CT scan thereby triggering motion artifacts. The structure is preferably part of the moving object and moves together with this object, such as, for example, blood vessels in an organ or bones or skeletal elements in the human body generally. The structure preferably extends with at least partially elongated extensions through the moving object, in particular through the organ to be depicted. In particular, the structure is a vessel, the skull, bones, such as, for example, ribs, or the like.

The CT data has at least one energy level of which at least one energy level is adapted to a structure in the moving object. 'Adapted' means that the energy level or several energy levels at which CT data is recorded is selected such that the structure stands out on the CT data due to a high contrast from the surrounding tissue and is hence easily identifiable. If the structure of iodine-contrasted blood vessels is imaged, an energy level of, for example, approximately 33 keV is suitable since the mass attenuation coefficient of iodine is maximum here, while absorption by water is relatively low. At this energy level, the vessels have an extremely high contrast against the surrounding tissue.

In a next step, the structure in the CT data at this energy level is identified, as described in more detail below. In particular, the structure identified in a time-resolved manner, i.e. the structure moving during the CT recording is tracked at least at one, in particular at several positional points. From this, a so-called motion vector field is calculated. A three-dimensional motion vector field represents the movement of the structure at a specific time point during the recording of the CT data, preferably in each case at one or more positional points within the structure. In particular, this motion vector field is created for several time points during the CT data recording time and is thus a four-dimensional motion vector field (the fourth dimension is the time).

This motion vector field is then used to perform motion correction of the recorded CT data and hence to calculate a motion-corrected CT image.

Compared to the algorithmic segmentation performed to date, the material decomposition enabled here by spectral CT recordings has the advantage that no, or only very little, computational effort is required and hence the time required to obtain the motion-corrected image is reduced. Furthermore, the structure can be isolated particularly robustly; the risk of errors during the segmentation of the structure in the moving object is reduced. The material composition preferably used in the invention is based on the spectral response of a specific chemical, which is naturally inherent and hence is not subject to the susceptibility to errors of segmentation algorithms, such as those required in the prior art.

The robust motion correction provided hereby now enables CT recordings to be taken with longer recording times or slower rotational speeds, if this is necessary. Furthermore, the robust motion correction enables sedation or even anesthesia to be dispensed with in the case of non-cooperative patients. Finally, the need for repeat scans is avoided and thus the X-ray dose delivered to the patient is reduced.

The structure is preferably identified by material decomposition. This method is based on the calculation of images depicting the spatial distribution of the material density of two or more materials from the spectral CT data. If one of the materials only occurs in the structure (for example iodine or calcium), this can be identified with virtually no further processing steps and, if necessary, extracted from the CT data. In one embodiment, segmentation can be performed during the material decomposition, in particular with a limit value, and the structure extracted from the CT data as a result.

According to an example embodiment, the structure is already identified in the sinograms of the CT data, i.e. the projection data, at the energy level(s) adapted to the structure. Hence, the structure, for example the blood vessel, can already be isolated from the surrounding tissue on the sinogram. This avoids errors in the subsequent image reconstruction. The identification is practically self-evident since the structure on the CT data with the energy level adapted to the structure has a significantly greater contrast than the surrounding tissue. It is optionally also possible to apply a slight limit-value segmentation in order to remove the surrounding tissue with gray values below the limit value—for example in the region of noise—reliably.

According to one embodiment, the structure is extracted from the sinograms of the CT data at a single energy level adapted to the structure. For example, the energy level adapted to the structure is one with which the structure absorbs or attenuates the photons particularly strongly so that excellent contrast between the structure and the surrounding tissue is already obtained with the CT data at a single energy level.

In another embodiment, the structure is extracted by weighted subtraction of the CT data at two different energy levels. This can, for example, be relevant for calcium, since calcium has no maximum mass attenuation coefficient. However, the difference in the attenuation rate of calcium and water is different at different energy levels. This effect can be used to greatly increase the contrast between calcium and water and hence the contrast between bone and the surrounding water-containing softer tissue by targeted weighted subtraction of the CT data at different energy levels. It is subsequently optionally possible also to perform limit-value segmentation in order to remove the surrounding tissue completely. The sinograms are also preferably used for the weighted subtraction, but if necessary, the reconstructed image data can also be used.

A motion vector field can be calculated from the CT data obtained in this way, preferably from the sinograms, which now only contains the moving structure.

In one possible embodiment, the motion vector field is calculated as follows: at least one time sequence of partial images is reconstructed from the CT data at the energy level adapted to the structure, in particular from the CT data, which now only contains the identified structure, by partial angle reconstruction and from this an in particular four-dimensional motion vector field is calculated. Partial-angle reconstruction means that it is not the sinogram data from the actually necessary angular range of 180° plus fan angle that are used, but only the sinograms from a small angular segment. For this reason, the image reconstruction is more susceptible to error, but this is compensated by reducing the image content to the identified structure only.

The partial images obtained in this way have good temporal resolution since they are were obviously recorded in a shorter time period than a complete scan of 180° plus fan angle would have needed. On the time sequence of partial images generated in this way, the structure can, for example, be tracked at specific defined landmarks or positional points from one image in the time sequence to the next, i.e. a specific positional point is tracked on the time sequence of images. Such methods are known as feature-tracking methods.

It is then possible to calculate a motion vector field for each partial image in the time sequence from the displacement of the respective positional point from one image to the next and the known time interval between the individual partial images. This results in a four-dimensional motion vector field.

The spatial density of the field can be adapted to the respective requirements; with coronary arteries, it is, for example, possible to set a positional point every 2-10 mm along the coronary artery. The time resolution of the time sequence of partial images is, for example, 5-50, in particular 8-20 ms. If the structure includes blood vessels, according to one advantageous embodiment, it is possible to determine a centerline through each blood vessel in each case.

The above passage describes the so-called PAMoCo method (motion compensation based on partial angle reconstructions), but the method according to at least one embodiment of the invention can also be advantageously be applied to any other algorithm for motion compensation.

In a preferred embodiment, the CT data at the energy level adapted to the structure is divided into several stacks of axial images, wherein the stacks are registered to one another with the aid of the identified structure. This has the advantage that each stack can be processed independently thus reducing motion artifacts from the respective movements during the acquisition of a stack. The stacks preferably overlap slightly in the axial direction. According to one embodiment, only short scan data acquired during one heartbeat is used for the reconstruction of each stack.

The stacks are preferably registered to one another with the aid of the identified and possibly extracted structure. The recording of CT data at the energy level adapted to the structure enables simple isolation of the structure and material composition and hence a simplified image with generally little image content. This facilitates the registration. As a result, adjacent staples can be registered to one another more robustly and easily and the risk of incorrect registration is reduced.

On the one hand, this facilitates the actual motion correction. In addition, in this way, at least one embodiment of the invention enables the recording of large continuous volumes, since large image volumes can be recorded in the Z direction. Even if the patient moves during the recording (for example in a spiral CT), the decomposition of the large recording volume into individual stacks and corresponding inventive processing of the individual stacks and the registration of adjacent stacks with the aid of the extracted structure enables a large image volume to be achieved without motion artifacts. This permits recording of large continuous volumes, which are better suited for purely diagnostic purposes.

In one embodiment, the reconstruction of the partial images can be facilitated by not using the sinogram data for the entire examination region. Instead, the CT data at the energy level adapted to the structures is first completely reconstructed to form a non-motion-compensated image. Despite motion artifacts, the structure should be to some extent identifiable on this image, in particular in the case of contrasted coronary arteries.

Following this, a region of interest (ROI) is defined around the structure, for example, in the case of a coronary artery, a tube surrounding the artery centerline. This region of interest should enclose all motion artifacts of the structure. Then, partial angle reconstruction is performed solely for this region of interest; sinogram data that do not belong to this region is ignored. This further improves the image quality of the time sequence of partial images. It is also possible to define several regions of interest for different parts of the structure.

According to a preferred embodiment, an individual region of interest is defined for each stack of axial images in that the region of interest containing the motion artifacts is defined around the structure. Then, the region of interest for each stack is in each case reconstructed by partial angle reconstruction to form a time series of partial images, wherein the sinogram data lying outside the region of interest is ignored.

The above passage describes the so-called PAMoCo method (motion compensation based on partial angle reconstructions), but the method according to the invention can also advantageously be applied to any other algorithm for motion compensation. In particular, partial angle reconstruction can also be performed for all the sinogram data.

The spectral CT data can include CT data at several energy levels. Herein, the motion vector field can be used for motion correction of the CT data at the energy level adapted to the structure or at another energy level. The former solution is particularly advantageous in angiographic applications in which only vessels are to be examined. The second application is, for example, advantageous when it is actually the soft tissue that is to be examined, but it is skeletal parts contained therein that form the structure used for the motion correction.

In some embodiments, the recording of the spectral CT data of the examination region with the possibly moving object is part of the method. However, the method can also be performed offline, in particular on any computer provided with the recorded spectral CT data.

The method of various embodiments is designed to be performed on any computer, for example a personal computer, workstation, network computer, mobile device or in the cloud. The performance of the method typically requires a computational unit, for example a CPU, to reconstruct the image data and to calculate the motion vector field etc., and a data memory to store the spectral CT data and the motion field. Such a computer can be part of the console of a CT device but can also be independent thereof.

In some embodiments, it is expedient, simultaneously with the recording of the spectral CT data of the examination region, to record an electrocardiogram (ECG) of the patient being examined, in particular when the moving object is the heart. This enables triggering or gating of the recording after the heartbeat, in particular the recording of data from specific cardiac phases or for it to be ensured that the necessary recordings have been made in each cardiac phase.

Possible applications of the method according to an embodiment of the invention are for example: computed tomography of the heart and the blood vessels using an iodine-containing contrast medium to isolate the vessels. Further possible applications are neuro-CT using calcium to isolate the skull, pediatric CT using calcium to isolate the skeleton, CT of the thorax and the pulmonary function using calcium in order to localized the ribs etc.

In one possible embodiment, the motion correction is, for example, performed with the following steps:
1. Image reconstruction using back-projection algorithms of the CT data at the energy level adapted to the structure. This obtains an image volume with motion artifacts.
2. The structure is identified on this volume. In the prior art, it was necessary to this end to perform algorithmic segmentation, for example using limit-value methods. The invention generally dispenses with this segmentation step since the moving structure is already optimally visualized.
3. Estimation of the movement by calculating motion vector fields. Various methods can be used for this.
4. Motion correction of the CT data by the motion vector field in either image space or sinogram space.

At least one embodiment of the invention is also directed at an energy-sensitive CT device configured to perform the method according to one of the preceding steps or embodiments. According to a preferred embodiment, the energy-sensitive CT device comprises a multi-energy detector, which is able to record spectral CT data at several different energy levels simultaneously. A so-called photon-counting detector is particularly preferable.

This new technology is based on special materials that convert X-rays directly into electrical pulses with a voltage correlated with the energy of the incoming photon. As a result, it is theoretically possible to count individual photons and hence to record a complete energy spectrum. However, the method can also be performed with the dual-energy CTs already in use with which photons are emitted at two different energy levels and recorded by two separate detectors. It is advantageous if the CT device permits simultaneous recording of CT data at different energies at the same position simultaneously. Therefore, embodiments of CT devices with which two different X-ray tube/detector systems are operated offset by 90° are less preferable.

Figure 1:
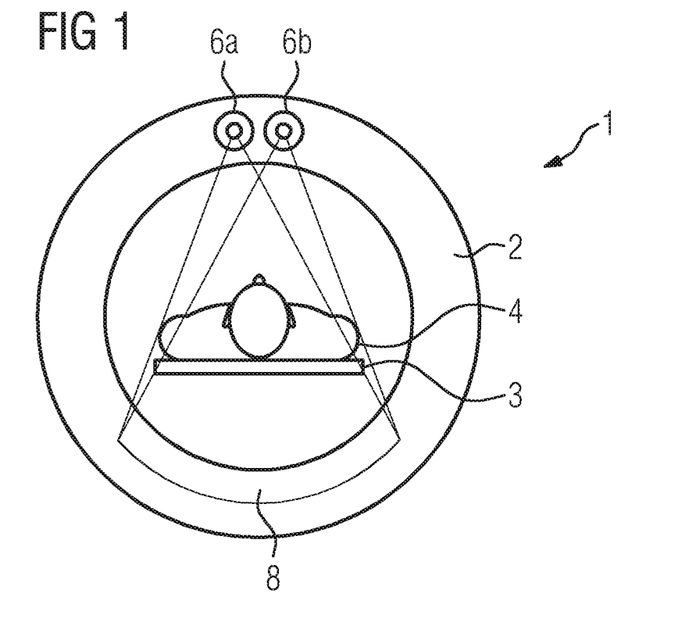
FIG. 1 shows a first embodiment of a CT device according to an embodiment of the invention.

FIG. 1 shows a schematic cross section through a CT device 1 that permits rapid switching between two different energy levels. In the gantry 2, there is a patient bench 3 with a patient 4 lying thereupon. Two different X-ray sources 6a, 6b alternately emit X-rays at different energies, for example 80 and 140 keV, or 33 and 80 keV, in rapid alternation. The X-ray detector 8 is switched accordingly and in each case assigns the detected photons to the different energy levels. Here, only one detector is required to record several energy levels.

Figure 2:
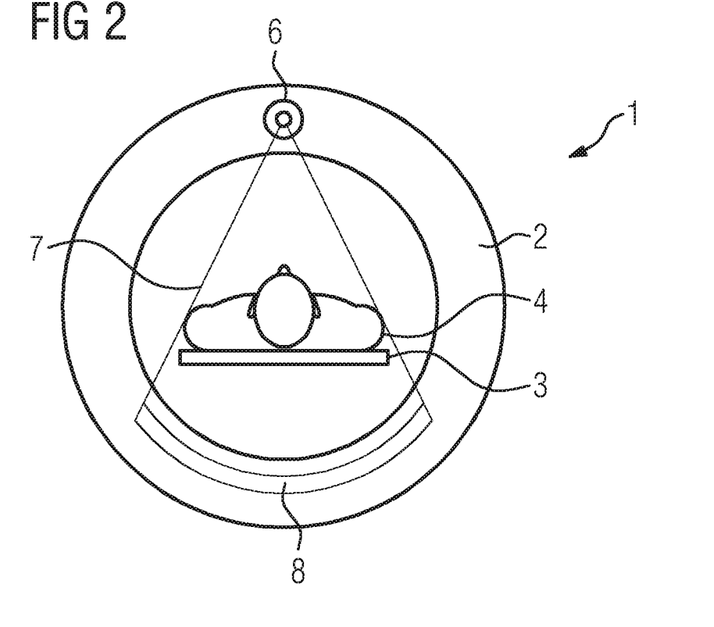
FIG. 2 shows a second embodiment of a CT device according to an embodiment of the invention.

FIG. 2 shows another embodiment with only one X-ray source 6 which photons emits photons at different energy levels. To this end, the detector 8 is configured to detect different energy levels, for example using split beam technology in which the spectrum is divided into high-energy and low-energy spectra. The use of a photon-counting detector 8 is also conceivable. The X-rays emitted by the X-ray source 6 are generally fan-shaped 7. The X-ray device 1 can be a spiral CT.

Figure 3:
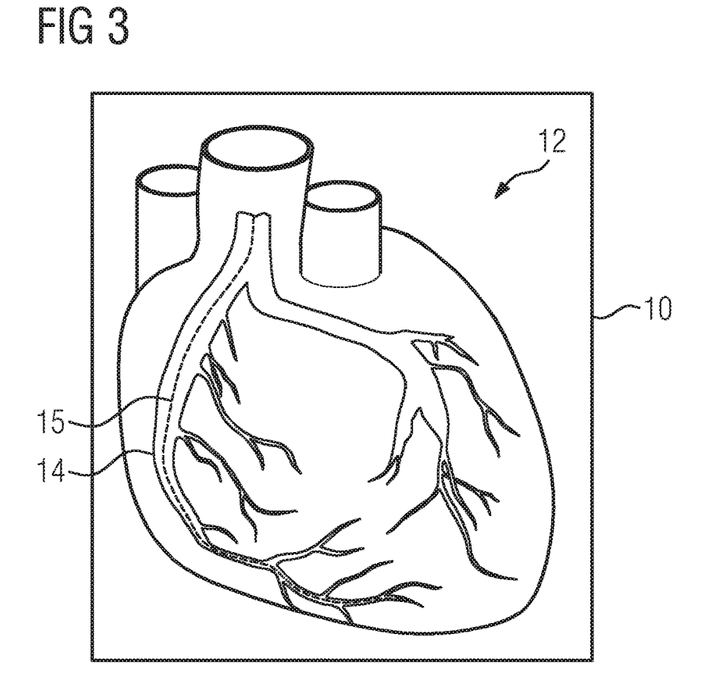
FIG. 3 shows a schematic view of the heart with segmented coronary arteries.

FIG. 3 shows, by way of example, a moving object 12, here the human heart, in an examination region 10. As a rule, the examination region 10 is the field of view of a CT device, i.e. it extends over a greater width in the axial direction than depicted on the image. The coronary arteries 14 are run inside the cardiac wall. If these arteries are contrasted in the known way with an iodine-containing contrast medium and simultaneously spectral CT data recorded at an energy level in which iodine has a particularly high mass attenuation coefficient, CT data can be recorded that practically selectively exclusively shows the coronary vessels 14.

According to one embodiment, therefore, it is possible, to reconstruct a non-motion-governed image volume from the spectral CT data and then to identify or segment the coronary arteries, as indicated here by hatching. Furthermore, it is also possible to determine a centerline 15 of the vessel, which is shown here as a dashed line. Ideally, the segmentation is performed by way of a short-scan reconstruction of the entire volume.

Figure 4:
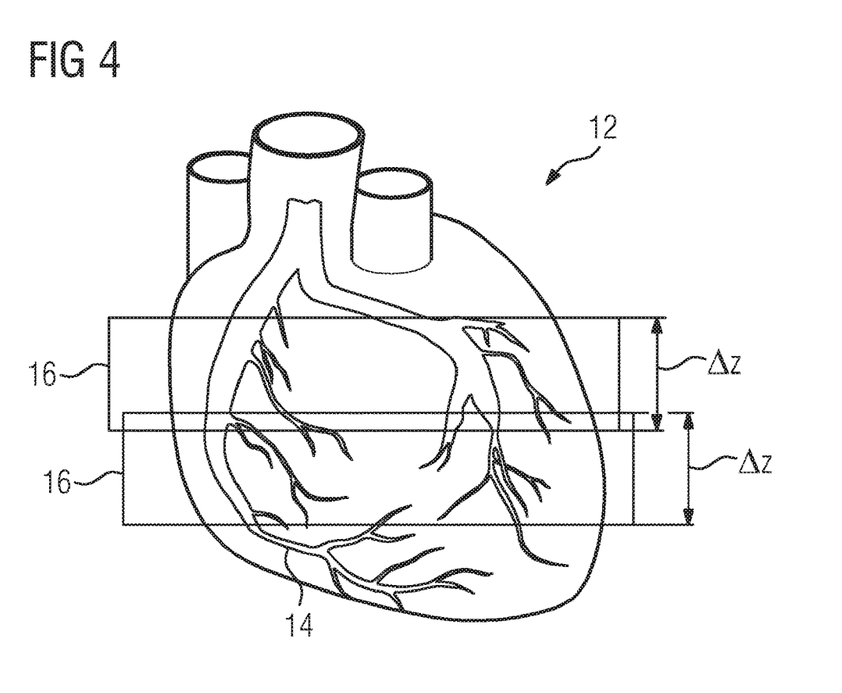
FIG. 4 shows a schematic view of the heart with two stacks of axial images.

As shown in FIG. 4, in a next step, the volume can be divided into several overlapping stacks 16, wherein each stack 16 has the extent $\Delta z$ in the longitudinal direction of the device. Preferably, the reconstruction of each stack is performed using only short scan data recorded during one heartbeat. The CT data in each stack is preferably processed independently.

Figure 5:
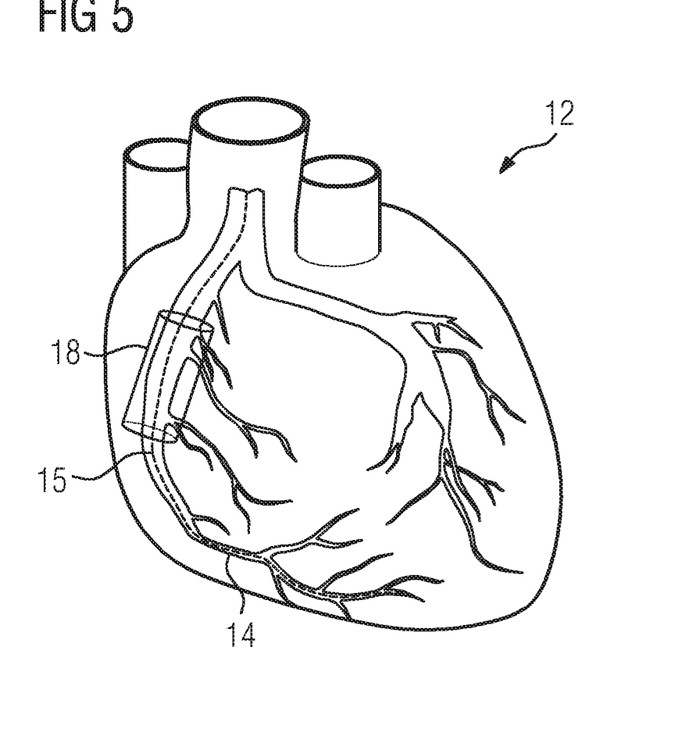
FIG. 5 shows a schematic view of the heart with a region of interest plotted around a coronary artery.

In a further step, a region of interest 18 can in particular be defined for each stack 16, as shown in FIG. 5. In the case of coronary arteries, this region is preferably formed by placing a tube 18 with a specific radius around the centerline 15 of the coronary artery 14 that has already been identified on the non-motion-corrected image. This region 18 should contain all motion artifacts generated by the movement of the coronary arteries 14. The radius of the tube 18 can optionally be defined in advance.

The definition of a region of interest 18 is optional, the method could also process the complete image volume.

Figure 6:
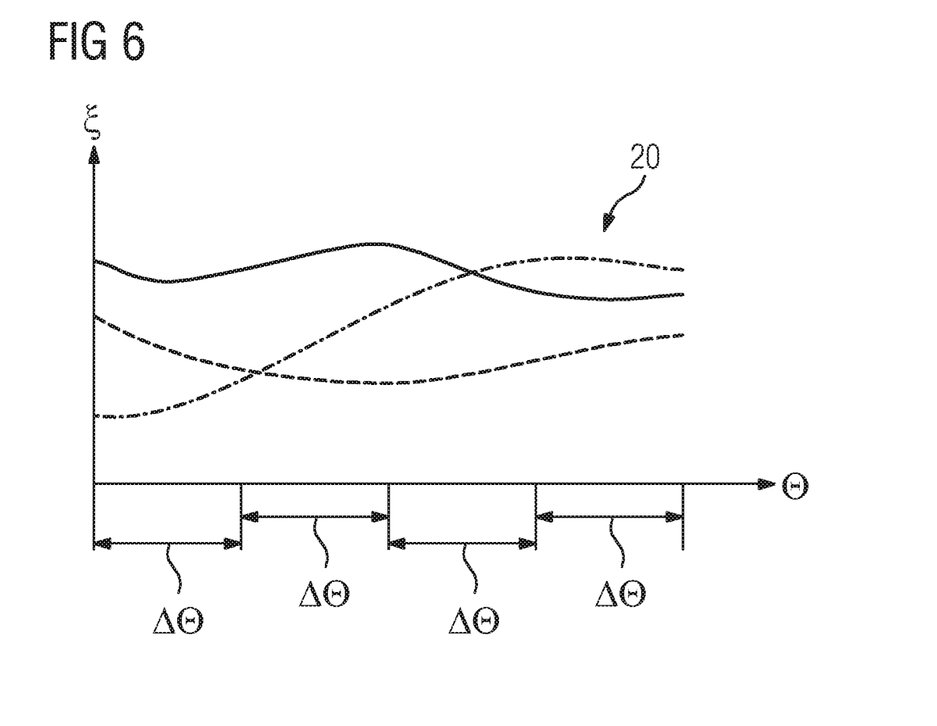
FIG. 6 shows a sinogram data of CT data at the energy level adapted to the structure divided into angular sections for partial angle reconstruction.

In a next step, preferably a time sequence of partial images is reconstructed by means of partial angle reconstruction. To this end, it is useful, as shown schematically in FIG. 6, for the sinogram data 20 to be divided into a number of overlapping sectors $\Delta \theta$. $\Delta \theta$ stands for the partial angle and the data from each $\Delta \theta$ is reconstructed to form a partial image. Herein, it is preferable for exclusively the sinogram data from the region of interest 18 to be used. A corresponding motion vector field can be calculated from the partial images constructed in this way.

Figure 7:
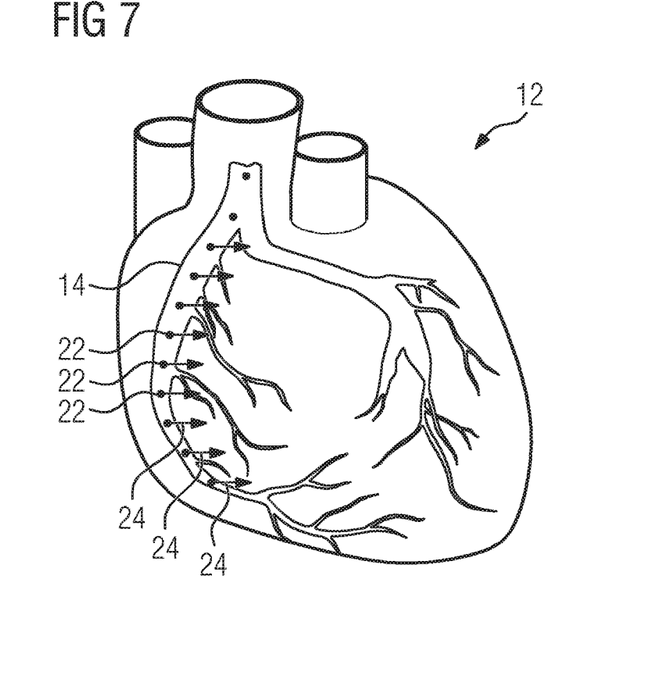
FIG. 7 shows a schematic view of a heart with motion field.

To this end, FIG. 7 shows a number of positional points 22 positioned in each case along the coronary artery 14. Each positional point 22 is tracked over the time sequence of the partial images and then a motion vector 24 ascertained for each partial image, i.e. for each point of the time sequence. The four-dimensional motion vector field is obtained from these motion vectors.

The motion vector field is then used to correct either the uncorrected image volume of the heart 12 shown in FIG. 3 or the sinogram data appropriately in order to obtain a motion-corrected CT image.

Figure 8:
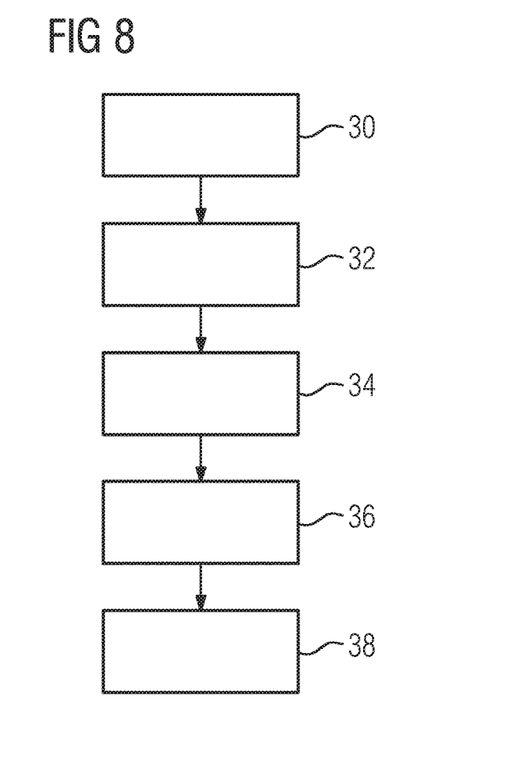
FIG. 8 shows a flow diagram of the method according to an embodiment of the invention.

FIG. 8 is another overview of the method according to an embodiment of the invention. In a step 30, spectral CT data of an examination region 10 with a moving object 12 is provided or recorded, wherein this includes CT data at at least one energy level, which is adapted to a structure 14 in the moving object 12.

In step 32, the structure is identified in the CT data and one or more image volumes, for example by partial angle reconstruction. In step 34, a motion vector field is calculated therefrom. This is used in step 36 for motion correction of the spectral CT data so that a motion-corrected CT image can be provided in step 38.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for motion correction of a computed tomography image, comprising:
   provisioning spectral CT data of an examination region with a moving object, the spectral CT data being recorded with an energy-sensitive CT device and including CT data at at least one energy level, and the at least one energy level of the CT data being adapted to a structure in the moving object;
   identifying the structure in the CT data at at least one energy level, of the at least one energy level, adapted to the structure;
   calculating a motion vector field of the structure identified; and
   motion correcting the spectral CT data by the motion vector field calculated to produce a motion-corrected CT image, wherein the structure is a part of a skeleton including a skull and wherein the at least one energy level adapted to the structure lies in a region in which water and calcium have very different mass attenuation coefficients.

2. The method of claim 1, wherein the identifying of the structure includes identifying the structure in sinograms of the CT data at the at least one energy level adapted to the structure.

3. The method of claim 2, wherein the spectral CT data includes CT data at several energy levels and wherein the motion vector field is used for motion correction of the CT data at the at least one energy level adapted to the structure or at another energy level.

4. The method of claim 1, wherein the identifying of the structure includes identifying the structure by material decomposition.

5. The method of claim 1, wherein the identifying of the structure includes identifying the structure in the CT data at a single energy level adapted to the structure.

6. The method of claim 1, wherein at least one time sequence of partial images is reconstructed from the CT data at the at least one energy level adapted to the structure and wherein the motion vector field is calculated from the at least one time sequence of partial images.

7. The method of claim 6, wherein a non-motion-compensated image is reconstructed from the CT data at the at least one energy level adapted to the structure and a region of interest is defined on the non-motion-compensated image that includes the structure or a part of the structure, and wherein the at least one time sequence of partial images is reconstructed solely from the CT data belonging to the region of interest.

8. The method of claim 6, wherein at least one time sequence of partial images is reconstructed from the CT data at the at least one energy level adapted to the structure by partial angle reconstruction and wherein the motion vector field is calculated from the at least one time sequence of partial images.

9. The method of claim 8, wherein a non-motion-compensated image is reconstructed from the CT data at the at least one energy level adapted to the structure and a region of interest is defined on the non-motion-compensated image that includes the structure or a part of the structure, and wherein the at least one time sequence of partial images is reconstructed solely from the CT data belonging to the region of interest.

10. The method of claim 1, wherein the CT data is divided into several stacks of axial images, and wherein the several stacks are registered to one another with aid of the identified structure.

11. The method of claim 1, wherein the spectral CT data includes CT data at several energy levels and wherein the motion vector field is used for motion correction of the CT data at the at least one energy level adapted to the structure or at another energy level.

12. The method of claim 1, wherein the structure is an iodine-contrasted blood vessel.

13. The method of claim 12, wherein the iodine-contrasted blood vessel is a coronary artery.

14. The method of claim 1, further comprising:
   recording spectral CT data of the examination region with the moving object with an energy-sensitive CT device, wherein the spectral CT data includes CT data at at least one energy level and wherein at least one energy level of the at least one energy level is adapted to a structure in the moving object.

15. The method of claim 1, wherein the identifying of the structure includes identifying the structure by weighted subtraction of the CT data at two different energy levels.

16. An energy-sensitive CT device, comprising:
   at least one processor, configured to
      provision spectral CT data of an examination region with a moving object, the spectral CT data being recorded with an energy-sensitive CT device and including CT data at at least one energy level, and the at least one energy level of the CT data being adapted to a structure in the moving object,
      identify the structure in the CT data at the at least one energy level adapted to the structure,
      calculate a motion vector field of the structure identified, and
      motion correct the spectral CT data by the motion vector field calculated to produce a motion-corrected CT image, wherein the structure is a part of a skeleton including a skull and the at least one energy level adapted to the structure lies in a region in which water and calcium have very different mass attenuation coefficients.

17. The energy-sensitive CT device of 16, further comprising:
a multi-energy detector, to record spectral CT data at several different energy levels simultaneously.

18. The energy-sensitive CT device of 17, wherein multi-energy detector is a photon-counting detector.

19. The energy-sensitive CT device of 16, wherein the at least one processor is configured to identify the structure in the CT data at a single energy level adapted to the structure.

20. The energy-sensitive CT device of 16, wherein the spectral CT data includes CT data at several energy levels and wherein the at least one processor is configured to identify the structure in the CT data at the at least one energy level adapted to the structure or at another energy level.

\* \* \* \* \*